United States Patent
Hattori et al.

(10) Patent No.: US 6,777,024 B2
(45) Date of Patent: Aug. 17, 2004

(54) METHOD OF MANUFACTURING GAS SENSORS

(75) Inventors: Akiyoshi Hattori, Yahata (JP); Nobuyuki Yoshiike, Ikoma (JP); Yoshikatsu Inoue, Kusatsu (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/269,135

(22) Filed: Oct. 11, 2002

(65) Prior Publication Data

US 2003/0037593 A1 Feb. 27, 2003

Related U.S. Application Data

(62) Division of application No. 09/774,472, filed on Jan. 31, 2001, now abandoned.

(51) Int. Cl.[7] .................................................. B05D 5/12
(52) U.S. Cl. ................... 427/58; 427/126.3; 427/126.5; 427/372.2
(58) Field of Search ............................... 427/58, 126.3, 427/126.5, 372.2

(56) References Cited

U.S. PATENT DOCUMENTS

| | | |
|---|---|---|
| 4,224,280 A | 9/1980 | Takahama et al. |
| 5,003,812 A | 4/1991 | Yagawara et al. |
| 5,215,643 A | 6/1993 | Kusanagi et al. |
| 5,360,528 A | 11/1994 | Oh et al. |
| 5,609,096 A * | 3/1997 | Kwon et al. .................. 99/468 |

FOREIGN PATENT DOCUMENTS

| | | | |
|---|---|---|---|
| JP | 53497 | * | 5/1974 |
| JP | 116894 | * | 9/1981 |
| JP | 75247 | * | 4/1987 |
| JP | 61380 | * | 3/1991 |
| JP | 293972 | * | 10/1994 |
| JP | 08271465 | | 10/1996 |
| JP | 2875174 | | 1/1999 |

* cited by examiner

Primary Examiner—Brian K. Talbot
(74) Attorney, Agent, or Firm—RatnerPrestia

(57) ABSTRACT

A gas sensor characterized in that the gas sensor has at least:
  an insulating substrate;
  a pair of thin film electrodes which are spaced apart at a given interval and provided on the insulating substrate;
  a thin film gas sensitive layer which is provided on both the substrate and the thin film electrodes, the gas sensitive layer containing a given material as main ingredient; and
  a pair of thick film electrodes which is correspondingly positioned over the pair of thin film electrodes and provided on the thin film gas sensitive layer,
  wherein the thin film electrodes and the thick film electrodes are formed so as to sandwich portions of the thin film gas sensitive layer between the two types of electrodes.

7 Claims, 5 Drawing Sheets

METHOD OF MANUFACTURING GAS SENSORS

This application is a divisional of U.S. patent application Ser. No. 09/774,472, filed Jan. 31, 2001 now abandoned.

BACKGROUND OF THE INVENTION

1. Field of the Invention

The present invention relates to gas sensors and the manufacturing method thereof to determine freshness and/or putridity for vegetables or fruits by providing high sensitivity and high selectivity to low levels of gases, such as ethylene, ethanol, mercaptans, and amines, released from vegetables or fruits.

2. Related Art of the Invention

The freshness of foods or drinks is determined subjectively through vision, taste and sense of throat, thereby making the determination more or less vague. However, technical efforts are actively being made to develop semiconductor gas sensors for determining freshness. As shown in FIGS. 6 to 9, a semiconductor gas sensor is generally composed of an insulating substrate 1, a pair of electrodes 12, and a gas sensitive layer 13. Each of the semiconductor gas sensors in FIGS. 6 and 7 is configured by placing the pair of electrodes 12 on the insulating substrate 1 and forming the gas sensitive layer 13 on the insulating substrate 1 and also on the pair of electrodes 12. Each of the semiconductor gas sensors in FIGS. 8 and 9 is configured by forming the gas sensitive layer 13 on the insulating substrate 1 and placing the pair of electrodes 12 on the gas sensitive layer 13. In FIGS. 6 to 9, the pair of electrodes 12 indicates thick film electrodes.

A semiconductor gas sensor has recently been developed to sense trimethylamine, a malodorous component emitted from raw fish, for determining freshness for the fish. Oxide semiconductors based on titanium dioxide are commonly used as a sensitive material for the purpose described above, wherein addition of metal catalyst components to the titanium dioxide improves the sensitivity of the sensor. In this case, the sensitivity of the sensor depends on action and dispersed state of the catalyst and the thickness of the sensitive film, and the type of catalyst components and the amount of their addition play an important role in improving catalytic action described above. In addition to use of titanium dioxide as a sensitive material as mentioned before, indium oxide supplemented with magnesium is under study as sensitive material of a gas sensor for trimethylamine, wherein atomic control by addition of 5 mol % of magnesium oxide to indium oxide reduces electron density, thereby increasing resistance of the sensor in air to make it more sensitive. However, the study of sensitivity of this type of gas sensor for trimethylamine is still at an early stage to apply, and what is worse, too power-consuming to make its mass production feasible.

For vegetables, which emit sulfides gas (mercaptans) unlike trimethylamine coming out from raw fish, a sensor with an excellent sensitivity to determine freshness for vegetables has already been developed. Japanese Patent No. 2875174 describes a method of manufacturing a sensor to determine freshness for vegetables, comprising the steps of adding a given amount of palladium powders to tin oxide powders, mixing them, and then crushing them; calcining the crushed powder mix of tin oxide and palladium at a given temperature for a given time, and then mixing it with an organic material to make paste; coating the paste onto the electrode surface on the substrate to form a sensitive film; and drying the coating and then sintering it at a given temperature for a given time, thereafter connecting a lead wire to the electrode surface.

It has become clarified that a trace amount of ethylene, ethanol or aldehydes is emitted even from fresh vegetable or fruit, while mercaptans are emitted as vegetable or fruit begins to rot and amines, such as ammonia, are emitted as fruit begins to rot. It has also become clarified that sensing a gas, such as ethylene, ethanol or aldehydes is effective for determining freshness for vegetable or fruit, while sensing mercaptans or amines, such as ammonia, is suitable for determining putridity for vegetable or fruit. However, for the conventional type of sensors to determine freshness for vegetables described above, the sensitive film of which is formed by mixing tin oxide powders with a given amount of palladium powders, crushing and calcining them, and then mixing them with an organic material, resulting in production of paste, which is subsequently coated onto the electrode surface on the substrate, dried and sintered, it is difficult to detect one ppm level of ethylene, ethanol or aldehydes, which is necessary to determine freshness for vegetables, and also is difficult to detect one ppm level of mercaptans or amines which is necessary to determine the putridity for vegetables and fruits.

To describe it more specifically, in conventional examples illustrated in FIGS. 6 and 7, the gas sensitive layer 13 jammed between the thick electrodes 12, 12 is obviously formed of a correspondingly thick film due to the thickness of the electrodes in order to achieve a good electric joint. As a result, the problem that the sensor has a low sensitivity arises.

Further, in conventional examples illustrated in FIGS. 8 and 9, since the gas sensitive layer 13 is formed first on the substrate 1, followed by formation of the electrodes 12 over the gas sensitive layer 13, another problem arises that formation of the electrodes 12 may cause contamination of the gas sensitive layer 13 with some impurity.

SUMMARY OF THE INVENTION

The present invention is to eliminate the problems described above, and to provide gas sensors highly sensitive to such gas as ethylene, ethanol, aldehydes, mercaptans or amines, and the method of manufacturing them with a good reproducibility.

One aspect of the present invention is a gas sensor characterized in that said gas sensor comprises at least:
- an insulating substrate;
- a pair of thin film electrodes which are spaced apart at a given interval and provided on said insulating substrate;
- a thin film gas sensitive layer which is provided on both said substrate and said thin film electrodes, said gas sensitive layer containing a given material as main ingredient; and
- a pair of thick film electrodes which is correspondingly positioned over said pair of thin film electrodes and provided on said thin film gas sensitive layer,
- wherein said thin film electrodes and said thick film electrodes are formed so as to sandwich portions of said thin film gas sensitive layer between said two types of electrodes.

Another aspect of the present invention is a gas sensor characterized in that said gas sensor comprises at least:
- an insulating substrate;
- a pair of thin film electrodes which are spaced apart at a given interval and provided on said insulating substrate;

a thin film gas sensitive layer which is provided on both on said substrate and said thin film electrodes, said sensitive layer containing a given material as main ingredient; and a pair of thick film electrodes which is correspondingly positioned over said pair of thin film electrodes and provided in contact with said thin film electrodes.

As mentioned before, the gas sensor according to the present invention has a thinner film gas sensitive layer between the thin film electrodes and thus a better electric joint between the thin film gas sensitive layer and the thin film electrodes, compared with the conventional thick film type of gas sensor. This results in higher sensitivity, better stability and longer life of the gas sensor.

Problems associated with the conventional method, that is, adverse effects of the electrodes on the gas sensitive layer 3 in the manufacturing process, such as contamination, cannot arise in the method according to the present invention. It is because the thin film electrodes 2 have been formed before the thin film gas sensitive layer 3 is formed, raising no problems with the thin film electrodes 2. Although the thick film electrodes 4 are formed after the thin film gas sensitive layer 3, a portion of the gas sensitive layer 3 which is directly related to gas detection, namely, the portion P of the gas sensitive layer 3 placed between a pair of thin film electrodes 2 is considerably distant from the thick film electrodes 4, so that it is hardly affected adversely by formation of the thick film electrodes 4.

Even when a pair of thick film electrodes, corresponding to the pair of thin film electrodes, is provided on the thin film gas sensitive layer, as in examples shown in FIGS. 1 and 2, the thin film electrodes and thick film electrodes are configured so as to sandwich the thin film gas sensitive layer. Since electric current flows toward thinner electrodes, there exists virtually direct electric connections between the thin film electrodes and the thick film electrodes, indicating a good electric joint between the thin film electrodes and the thick film electrodes.

The method of manufacturing a gas sensor according to the present invention is characterized by providing a process of coating and then firing an organic solution containing a metal tin salt, an organic compound capable of coordinating to at least a tin, and an activator in order to form a thin film gas sensitive layer. Another method of manufacturing a gas sensor according to the present invention is characterized by providing a process of coating and then firing a paste consisting of a metal tin soap, an activator, and an organic solution containing a viscosity controller in order to form a thin film gas sensitive layer.

In the invention, an organic solution containing a metal tin salt, an organic compound capable of coordinating to at least a tin, and an activator is employed in order to form a thin film gas sensitive layer. Generally, a metal tin salt tends to be hygroscopic and/or hydrolyzable, and so it makes it difficult to produce gas sensitive layers of the same thickness or composition reproducibly. Therefore, an organic compound capable of coordinating to the tin is added to form coordination compounds by partial substitution, thereby achieving stabilization of the metal tin salt. In addition, a paste consisting of a metal tin soap, at least an activator, and an organic solution containing a viscosity controller can also be employed. A metal tin soap forms a micell with some organic solvents, resulting in increased viscosity of the solution so that it may be pasty. A viscosity controller helps to adjust the solution viscosity after it is dissolved in the organic solvent. An activator described above is one of metal salts other than tin salts. Addition of such a metal salt elevates the sensitivity and/or selectivity of the gas sensitive layer to a gas to be detected. A composition for producing a gas sensitive layer comprising an organic solution which contains a metal tin salt, a metal palladium salt, an organic compound capable of coordinating to a tin, and an activator, or a paste which consists of a metal tin soap, at least an activator, and an organic solution containing a viscosity controller is coated and then fired, resulting in reproducible production of gas sensitive layers where the activator is dispersed uniformly. As a result, more highly sensitive gas sensors, capable of detecting down to 1 ppm of different gases (ethylene, ethanol, aldehydes, mercaptans, and amines), can be manufactured, compared to the gas sensor to determine freshness for vegetables, produced in the process comprising the steps of adding a given amount of palladium powders to tin oxide powders, mixing them, and then crushing them; calcining the crushed powder mix of tin oxide and palladium at a given temperature for a given time, and then mixing it with an organic material to make paste; coating the paste onto the electrode surface on the substrate to form a sensitive film; and drying the coating and then sintering it.

DESCRIPTION OF SYMBOLS

1 Substrate
2 Thin film electrodes
3 Thin film gas sensitive layer
4 Thick film electrodes
12 Electrodes
13 Gas sensitive layer

PREFERRED EMBODIMENTS OF THE INVENTION

The embodiments of the invention will be described now.

Figure 1:
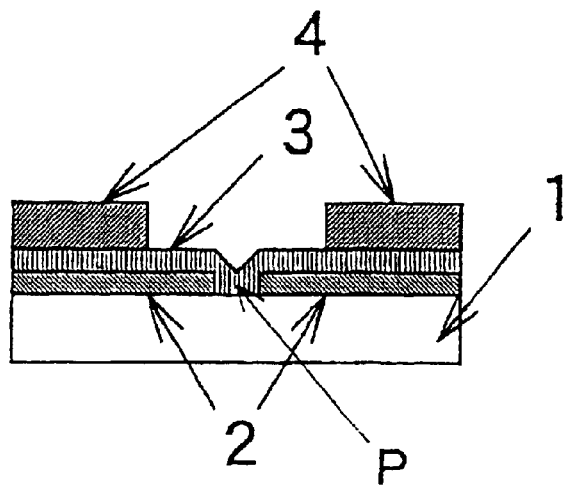
FIG. 1 is a schematic cross-sectional view, showing one example of gas sensors according to the invention.
Figure 2:
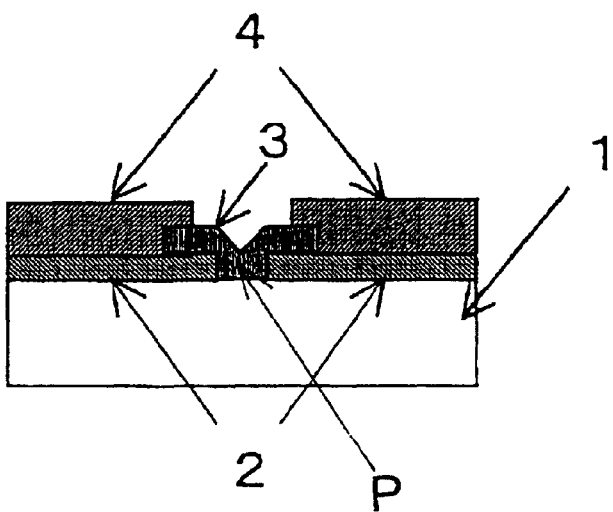
FIG. 2 is a schematic cross-sectional view, showing another example of gas sensors according to the invention.

FIGS. 1 and 2 are schematic cross-sectional views of typical gas sensors according to the invention, respectively. In FIGS. 1 and 2, reference numeral 1 denotes an insulating substrate, such as alumina, mullite or the like, reference numeral 2 denotes a thin film electrodes made of a metal, such as gold, silver or platinum, reference numeral 3 denotes a thin film gas sensitive layer consisting of metal oxides with a major component being tin oxide, and reference numeral 4 denotes a thick film electrodes made of a metal, such as gold, silver or platinum.

As the substrate 1, any material with an insulating surface and with heating function may be used. It is not limited with respect to material or configuration. However, the substrate has preferably a surface roughness between 0.01–1 µm in depth.

The thin film electrodes 2 and the thick film electrodes 4 serve to apply a voltage to the gas sensitive layer 3 to measure its resistance. They are not limited for material, configuration, pattern or manufacturing process. However, the thin film electrodes 2 are preferably 0.1–1 µm thick, while the thick film electrodes 4 are preferably 3–20 µm thick. As illustrated in FIG. 2, the thin film electrodes 2 may be in direct and partial contact with the thick film electrodes 4.

The thin film gas sensitive layer 3 is formed as below.

A composition for forming a gas sensitive layer is formed on the substrate, and then it is fired at a temperature of several hundred ° C. or more to form a thin film gas sensitive layer. The composition for forming a gas sensitive layer may be coated on the substrate by one of various methods, such as screen printing, roll coating, dip coating and spin coating, and preferably by dip coating or spin coating. The firing temperature is established in a range above the decomposition temperature of a composition for forming a gas sensitive layer and below the deformation temperature of the substrate, and preferably in the range of 400–800° C. A composition for forming a gas sensitive layer is prepared as below.

First, a metal tin salt is mixed with an organic compound which is capable of coordinating to a tin. A metal tin salt usable herein should have ligands to be replaced by an organic compound which is capable of coordinating to a tin. Examples are stannous chloride, tin acetylacetonate complex and tin 2-ethyl hexanoate.

Preferably, a metal palladium salt is readily decomposed by heat. Examples are palladium chloride and palladium acetylacetonate complex.

An organic compound which is capable of coordinating to a tin is necessary to stabilize a metal tin salt and to dissolve it in an organic solvent, through partial coordination to the tin. Examples include β-diketones, such as acetylacetone, etheralcohols, such as methoxyethanol, polyhydric alcohols, such as ethylene glycol, and condensation products of the polyhydric alcohols, such as diethylene glycol.

Subsequently, an organic solvent and an activator are added to the solution mentioned above, and the resulting organic solution undergoes heat treatment. Herein, an activator is a metal salt additive used to elevate sensitivity and gas selectivity for the gas sensitive layer. Examples include alkaline earth metal salts, such as metal magnesium salts, metal calcium salts, metal strontium salts or metal barium salts; transition metal salts, such as metal titanium salts, metal zirconium salts, metal vanadium salts, metal chromium salts, metal manganese salts, metal iron salts, metal cobalt salts, metal nickel salts or metal copper salts or; metal zinc salts; metal lead salts; metal cadmium salts; metal antimony salts; metal bismuth salts; and metal palladium salts, and preferably metal manganese salts, metal iron salts, metal cobalt salts, metal nickel salts, metal zinc salts and metal palladium salts. An activator compound should be relatively stable at room temperature by itself, but decomposed readily by heat treatment, whether it may be inorganic or organic. For example, inorganic salts include nitrates, sulfates and chlorides, whereas organic salts include carboxylates, dicarboxylates and acetylacetonate complexes. The organic solvent described above may be any solvent that can dissolve organic and inorganic compounds used according to the invention. Examples are alcohols, such as ethanol and isopropanol, ketones, such as acetone and diethyl ketone, tetrahydrofurane and the like. Further, if the activator mentioned above is hardly soluble at room temperature, the metal tin salt, the metal palladium salt, the organic compound capable of coordination to a tin and the organic solution containing the activator may be mixed and heated at the reflux temperature of the organic solution or just below the temperature.

The present invention will be described in more detail by the examples below.

EXAMPLE 1

A paste of the organic metal compound of gold was coated onto an alumina substrate 0.4 mm thick using screen printing and then dried, and subsequently it was fired at 800° C. to form thin film electrodes 0.3 µm thick as the first layer.

In a 1 l Erlenmeyer flask, to 8 g of stannous chloride (Chemical formula 1) 16 g of methoxyethanol was added and the mixture was mixed and made to be dissolved at room temperature. To the solution was added palladium chloride (Chemical formula 2) in an amount such that the value of the expression 1 is 5 mol % and 130 g of acetone, and the mixture was agitated and mixed to obtain the desired composition for forming a gas sensitive layer.

| $SnCl_2 \cdot 2H_2O$ | [Chemical formula 1] |
|---|---|
| $Pd/(Sn+Pd) \times 100$ | [Expression 1] |
| $PdCl_2 \cdot 2H_2O$ | [Chemical formula 2] |

The composition for forming a gas sensitive layer was applied on the alumina substrate 0.4 mm thick by dip coating, and then fired at 600° C. for 1 h to form the thin film gas sensitive layer which consisted of metal oxides containing tin oxide as main ingredient and had a thickness of 120 nm.

Gold paste for thick film printing was applied on the thin film gas sensitive layer 3 by screen printing and dried, and then fired at 600° C. to form thick film electrodes 8 µm thick as the second layer.

The sensor element thus produced was submitted for measurement to determine characteristics of response to ethylene gas. The sensor element was fixed in the quartz tube, heated at 400° C. by a heater, and then exposed to a flow of either air or air containing 1 ppm of ethylene alternately to measure a change in the resistance of the sensor element. Provided that the resistance of the sensor element when it is in a flow of air is denoted by RA, and its resistance 10 minutes after air is replaced by the ethylene-containing air is denoted by RG, RG/RA refers to the sensitivity of the sensor. The sensitivity thus obtained was found 0.70.

Figure 3:
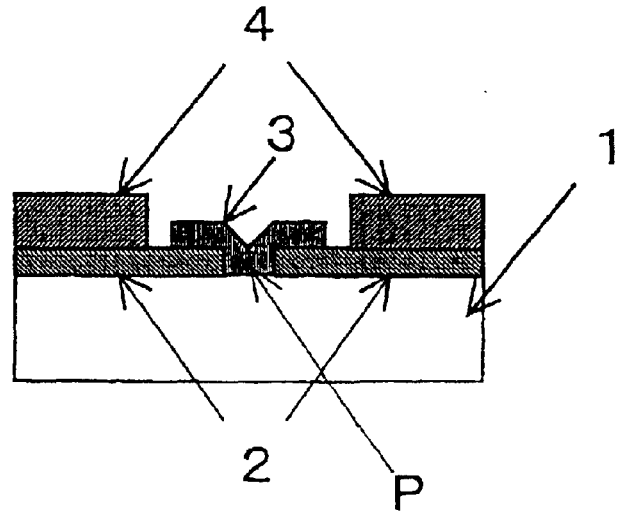
FIG. 3 is a schematic cross-sectional view, showing a further example of gas sensors according to the invention.

FIG. 3 is a schematic cross-sectional view, showing a further example of gas sensors according to the invention. In FIG. 3, reference numeral 1 denotes an insulating substrate, such as alumina, mullite or the like, reference numeral 2 denotes thin film electrodes made of a metal, such as gold, silver or platinum, reference numeral 3 denotes a thin film gas sensitive layer consisting of metal oxides with a major component being tin oxide, and reference numeral 4 denotes thick film electrodes made of a metal, such as gold, silver or platinum. The gas sensor here is different from the one in FIGS. 1 and 2 in that the thick film electrodes 4 are not formed on the thin film gas sensitive layer 3.

As the substrate 1, any material with an insulating surface and with heating function may be used. It is not limited with respect to material or configuration. However, the substrate has preferably a surface roughness between 0.01–1 μm in depth.

The thin film electrodes 2 and the thick film electrodes 4 mainly serve to apply a voltage to the gas sensitive layer 3 to measure its resistance. They are not limited with respect to material, configuration, pattern or manufacturing process. However, the thin film electrodes 2 are preferably 0.1–1 μm thick, while the thick film electrodes 4 are preferably 3–20 μm thick.

The thin film gas sensitive layer 3 is formed as below.

A composition for forming a gas sensitive layer is formed on the substrate, and then it is fired at a temperature of several hundred ° C. or more to form the thin film gas sensitive layer. The composition for forming a gas sensitive layer may be coated on the substrate by one of various methods, such as screen printing, roll coating, dip coating and spin coating, and preferably by screen printing. The firing temperature is established in a range above the decomposition temperature of the composition for forming a gas sensitive layer and below the deformation temperature of the substrate, and preferably in the range of 400–800° C. The composition for forming a gas sensitive layer is prepared as below.

First, an organic solvent is added to an activator to make a solution.

Herein, an activator is a metal salt additive used to elevate sensitivity and gas selectivity for the gas sensitive layer. Examples include alkaline earth metal salts, such as metal magnesium salts, metal calcium salts, metal strontium salts or metal barium salts; transition metal salts, such as metal titanium salts, metal zirconium salts, metal vanadium salts, metal chromium salts, metal manganese salts, metal iron salts, metal cobalt salts, metal nickel salts or metal copper salts; metal zinc salts; metal lead salts; metal cadmium salts; metal antimony salts; metal bismuth salts; and metal palladium salts. An activator compound should be relatively stable at room temperature by itself, but decomposed readily by heat treatment, whether it may be inorganic or organic. For example, inorganic salts include nitrates, sulfates and chlorides, whereas organic salts include carboxylates, dicarboxylates and acetyl acetonate complexes. The organic solvent described above should be able to dissolve both a metal tin soap and a viscosity controller, and is exemplified by etheralcohols, such as methoxyethanol and butylcarbitol, β-diketones, such as acetylacetone, esters, such as butylcarbitol acetate, and terpenoid solvents, such as α-terpineol.

Secondly, a viscosity controller is added to the organic solution and they are mixed.

The viscosity controller is any polymer to increase the viscosity of the organic solution, namely, with a thickening effect and is exemplified by polyvinyl pyrrolidinone and ethyl cellulose.

Finally, metal tin soap is added to the organic solution described above and they are mixed. Meanwhile, the viscosity controller may be added to the organic solution after the viscosity controller is mixed to the organic solution melted by heat.

Examples of the metal tin soap include tin 2-ethyl hexanoate and tin naphthenate.

The invention will be described below by more detailed examples, but it is not limited by the examples.

EXAMPLE 2

The paste of an organometallic gold compound was coated onto an alumina substrate 0.4 mm thick by screen printing and then dried, and subsequently fired at 800° C. to form thin film electrodes 2 of 0.3 μm thickness as the first layer.

Gold paste for thick film printing was applied on the thin film electrodes 2 of the first layer by screen printing and dried, and then fired at 800° C. to form thick film electrodes 6 μm thick as the second layer.

In a 100 ml beaker, palladium chloride (having the chemical formula 1, $SnCl_2.2H_2O$) as an activator was weighed so that the value of the expression Pd/(Sn+Pd)×100 may be 0–5 mol %, and then 4 g of butylcarbitol and 2 g of butylcarbitol acetate were added. They were mixed for some time. Then, 2 g of polyvinyl pyrrolidinone as viscosity controller was added and 6 g of tin 2-ethyl hexanoate (having the formula 3) ($Sn(OOCCH(CH_2CH_3)(CH_2)3CH_3)_2$) was also added. The whole matter was stirred and mixed to obtain the desired composition for forming a gas sensitive layer.

$$Sn(OOCCH(CH_2CH_3)(CH_2)3CH_3)_2 \qquad \text{[Chemical formula 3]}$$

The composition for forming the gas sensitive layer was applied on the alumina substrate 0.4 mm thick by screen printing and then fired at 700° C. for 1 h to form the thin film gas sensitive layer, which was 200 nm thick and consisted of metal oxides containing tin oxide as main ingredient.

Figure 4:
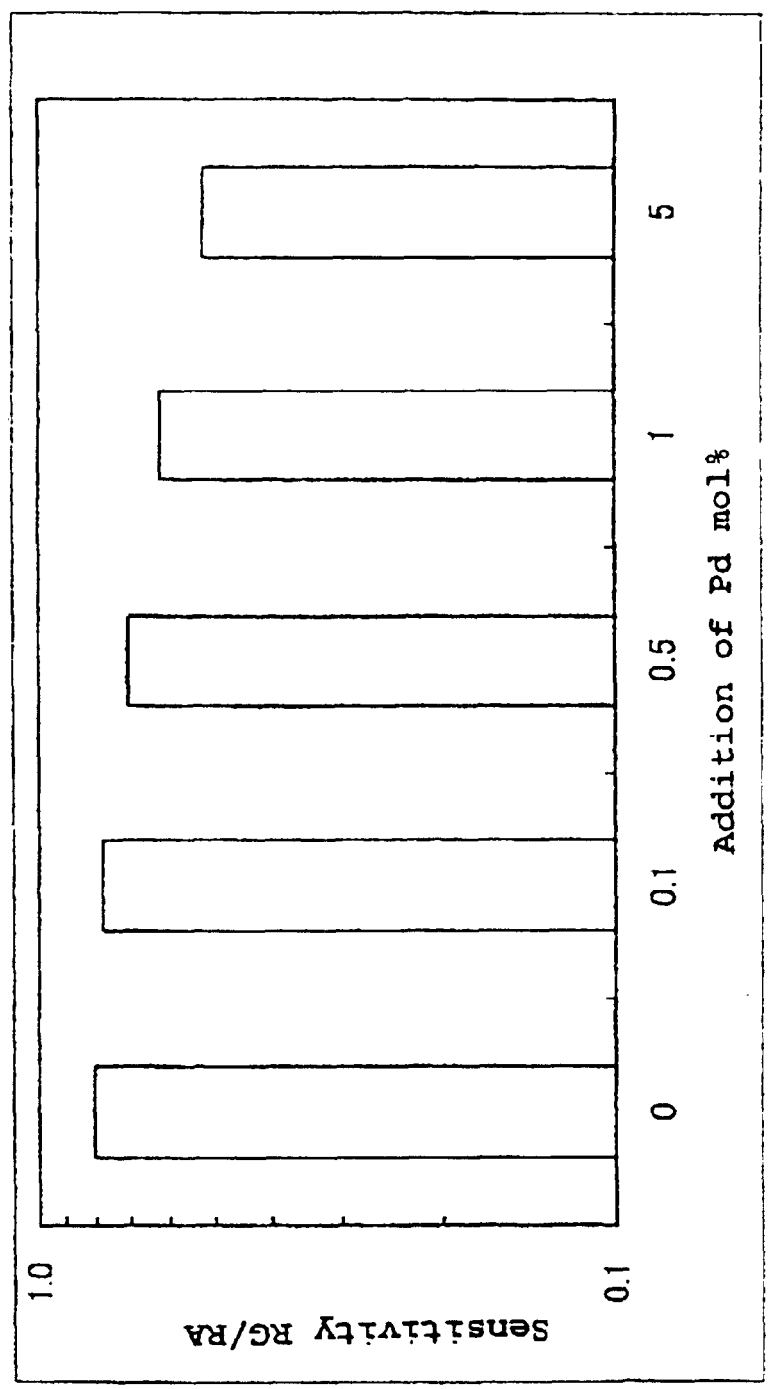
FIG. 4 is a graph showing a relation of the added amount of palladium to the sensitivity of the sensor in the example according to the invention.

Then, the sensor's sensitivity was measured for 1 ppm ethylene similarly as in Example 1. The temperature for measurement was 340° C. The results are shown in FIG. 4. In addition, the sensor's sensitivities for 1 ppm each of ethanol, acetaldehyde, methylmercaptan and ammonia were found to be 0.20, 0.30, 0.60 and 0.70, respectively.

EXAMPLE 3

In a 100 ml beaker, metal 2-ethyl hexanoate (M=Mn, Fe, Ni, Co, Zn) as an activator was weighed so that the value of the expression 2 could be 1 mol %, and then a solution of 1 g of ethyl cellulose in 12 g of butylcarbitol were added. They were mixed for some time. Finally, 6 g of tin 2-ethyl hexanoate $Sn(OOCCH(CH_2CH_3)(CH_2)_3CH_3)_2$ was added. The whole matter was stirred and mixed to obtain a desired composition for forming a gas sensitive layer.

$$M/(Sn+M)\times 100 \qquad \text{[Expression 2]}$$

The composition for forming the gas sensitive layer was applied on the alumina substrate 0.4 mm thick by screen printing and then fired at 700° C. for 1 h to form the thin film gas sensitive layer, which was 240 nm thick and consisted of metal oxides containing tin oxide as main ingredient.

Figure 5:
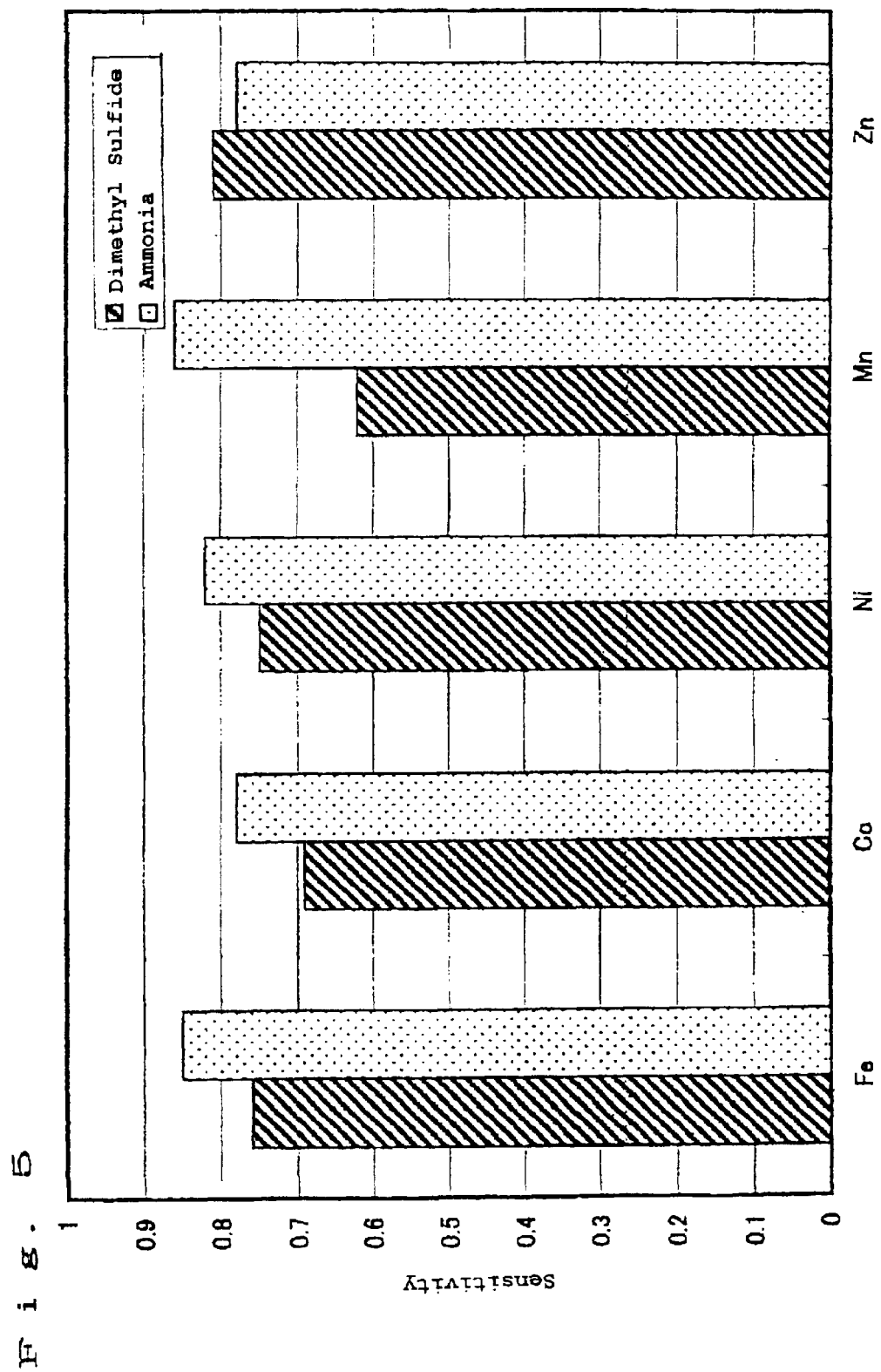
FIG. 5 is a graph showing effects of different metal additives on the sensitivity of the sensor in the example according to the invention.
Figure 6:
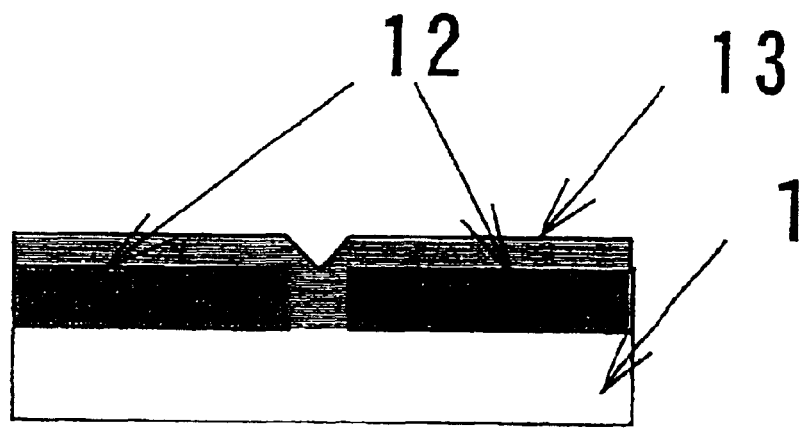
FIG. 6 is a schematic cross-sectional view of a conventional semiconductor gas sensor.
Figure 7:
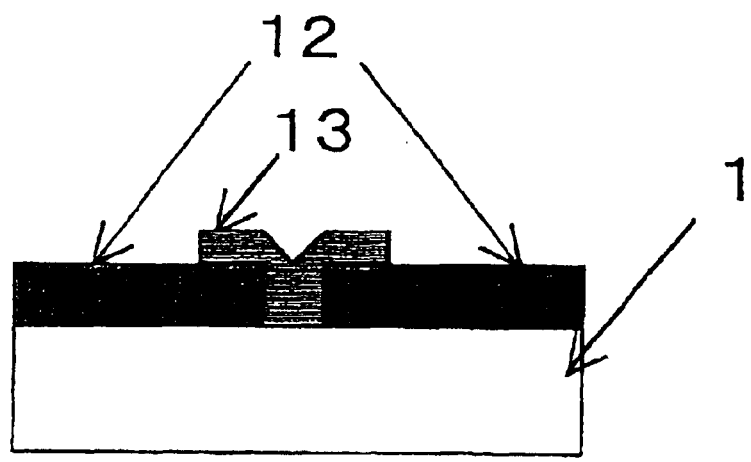
FIG. 7 is a schematic cross-sectional view of a conventional semiconductor gas sensor.
Figure 8:
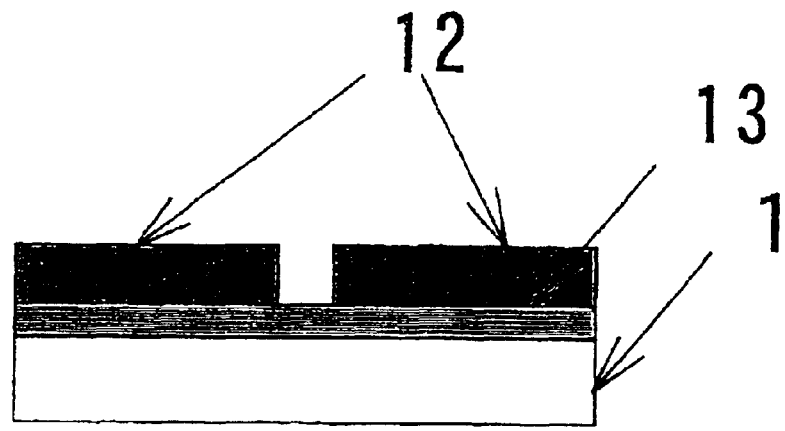
FIG. 8 is a schematic cross-sectional view of a conventional semiconductor gas sensor.
Figure 9:
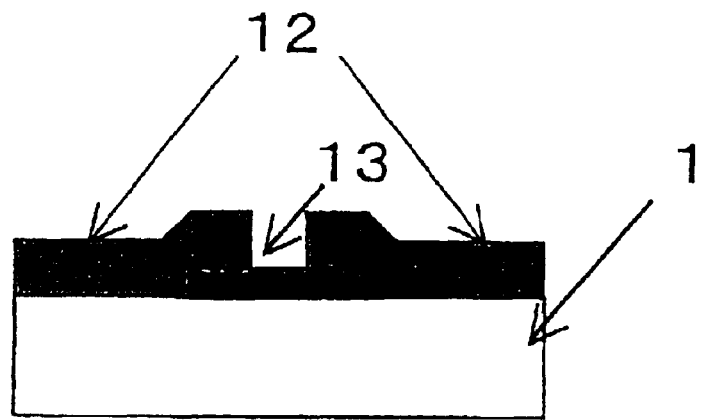
FIG. 9 is a schematic cross-sectional view of a conventional semiconductor gas sensor.

Then, the sensor's sensitivity was measured for 1 ppm each of dimethyl sulfide and ammonia similarly as in Example 1. The temperature for measurement was 340° C. The results are shown in FIG. 5.

The present invention provides gas sensors having high sensitivities to a low level of detectable gases (ethylene, ethanol, aldehydes, mercaptans and amines) released from vegetables and suitable for sensing freshness or putridity for vegetables.

What is claimed is:

1. A method of manufacturing a gas sensor characterized in that a process is provided wherein a thin film gas sensitive layer is formed by coating an organic solution comprising a metal tin salt, an organic compound capable of coordinating to at least a tin and an activator onto a substrate, and then by firing said solution, wherein said organic compound capable of coordinating to tin is at least one compound selected from the group consisting of etheralcohols.

2. The method of manufacturing a gas sensor according to claim 1 characterized in that said metal tin salt is at least one compound selected from the group consisting of stannous chloride, tin acetylacetonate complex and tin 2-ethylhexanoate.

3. The method of manufacturing a gas sensor according to claim 1 or claim 2 characterized in that said activator has at least one element selected from the group consisting of palladium, iron, nickel, manganese, cobalt and zinc, said activator being at least one compound selected from the group consisting of metal chlorides, metal acetylacetonate complexes and metal soaps.

4. The method of manufacturing a gas sensor according to claim 1 or claim 2 in which said organic compound capable of coordinating to a tin is methoxy ethanol.

5. A method of manufacturing a gas sensor characterized in that a process is provided wherein a thin film gas sensitive layer is formed by coating a paste comprising an organic solution comprising a metal tin soap, an activator and polyvinyl pyrrolidinone onto a substrate, and then by firing said paste.

6. The method of manufacturing a gas sensor according to claim 5 characterized in that said metal tin soap is selected from the group consisting of tin 2-ethylhexanoate, tin naphthenate, and mixtures thereof.

7. The method of manufacturing a gas sensor according to claim 5 or claim 6 characterized in that said activator has at least one element selected from the group consisting of palladium, iron, nickel, manganese, cobalt and zinc, said activator being at least one compound selected from the group consisting of metal chlorides, metal acetylacetonate complexes and metal soaps.

* * * * *

UNITED STATES PATENT AND TRADEMARK OFFICE
CERTIFICATE OF CORRECTION

PATENT NO. : 6,777,024 B2
DATED : August 17, 2004
INVENTOR(S) : Akiyoshi Hattori et al.

It is certified that error appears in the above-identified patent and that said Letters Patent is hereby corrected as shown below:

<u>Title page,</u>
Insert Item -- [30] Foreign Application Priority Data
     Jan. 31, 2000   [JP]    Japan   23104/2000 --.

Signed and Sealed this

Nineteenth Day of April, 2005

JON W. DUDAS
*Director of the United States Patent and Trademark Office*